United States Patent [19]

Kao et al.

[11] 4,383,117

[45] May 10, 1983

[54] PROCESS FOR PRODUCING SUBSTITUTED PYRROLES

[75] Inventors: James T. F. Kao; Everett M. Marlett, both of Baton Rouge, La.

[73] Assignee: Ethyl Corporation, Richmond, Va.

[21] Appl. No.: 317,156

[22] Filed: Nov. 2, 1981

[51] Int. Cl.$^3$ .......................................... C07D 207/34
[52] U.S. Cl. ...................................................... 548/531
[58] Field of Search .................... 260/326.46; 548/531

[56] References Cited

U.S. PATENT DOCUMENTS 3,752,826  8/1973  Carson ............................ 260/326.3
3,865,840  11/1975  Carson ........................... 260/326.46

FOREIGN PATENT DOCUMENTS 2034304  6/1980  United Kingdom .

OTHER PUBLICATIONS

Fischer et al., Die Chemie Des Pyrroles, Edward Brothers, Inc., Ann Arbor, Mich., (1943), pp. 5, 6, 233 & 234.

Gowan et al., Name Index of Organic Reactions, Longmans, Green and Co., Ltd., N.Y., (1960), p. 116.

Jones et al., The Chemistry of Pyrroles, Academic Press, Inc., N.Y., (1977), pp. 59 & 104.

Krauch et al., Organic Name Reactions, John Wiley and Sons, Inc., N.Y. (1964), p. 211.

Primary Examiner—Richard Raymond
Attorney, Agent, or Firm—Donald L. Johnson; John F. Sieberth; Patricia J. Hogan

[57] ABSTRACT

A process for the preparation of alkyl 1,4-dimethyl-3-ethoxycarbonylpyrrole-2-acetate compounds by reacting in a solvent a diloweralkyl acetone dicarboxylate, a chloromethyl lower alkyl ketone and anhydrous loweralkylamine.

6 Claims, No Drawings

PROCESS FOR PRODUCING SUBSTITUTED PYRROLES

BACKGROUND

This invention relates to a process for producing substituted pyrroles, especially pyrrole-2-acetic acids and derivative compounds thereof. More particularly, the process of this invention is concerned with processes which produce 1,4-diloweralkyl-3-loweralkoxycarbonyl-pyrrole-2-acetate which is a useful intermediate for analgesic and anti-inflammatory pharmaceutical compounds.

It has been found difficult in the past to substitute pyrrole rings, which already contain substituents at other positions on the ring, at the 4-position because of steric hindrance and ring deactivation. Thus, Carson, U.S. Pat. Nos. 3,752,826 and 3,865,840, teach the preparation of certain 4-substituted 5-aroyl-pyrrole alkanoic acids and the corresponding salts, esters, nitriles, amides and substituted amides thereof represented by the formulas:

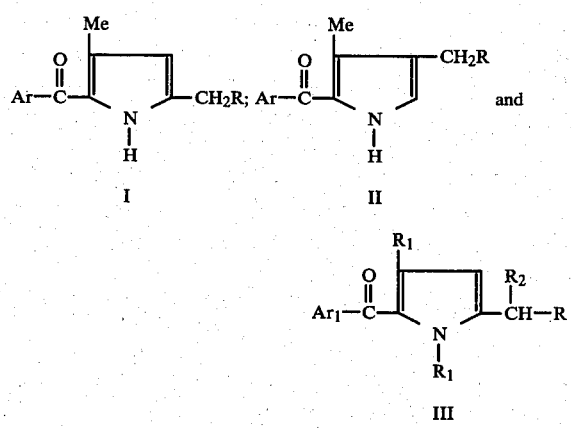

wherein:
Ar represents a member selected from the group consisting of phenyl, monosubstituted phenyl and polysubstituted phenyl, each substituent of said substituted phenyls being a member selected from the group consisting of halo, lower alkyl and lower alkoxy;
$Ar_1$ represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano, and methylthio;
R represents a member selected from the group consisting of COOH, COO-(lower alkyl), $CONH_2$, CONH-(lower alkyl) and CON-(lower alkyl)$_2$;
$R_1$ represents lower alkyl;
$R_2$ represents a member selected from the group consisting of hydrogen and lower alkyl, provided that when said Ar is a member of the group consisting of nitrosubstituted phenyl, then, with regard to Formula III, $R_2$ is hydrogen;
Me is methyl;
and the non-toxic, therapeutically acceptable salts of such acids, such as are obtained from the appropriate organic and inorganic bases. According to Carson, supra, the 4-substituted 5-aroyl-pyrrole alkanoic acids must be obtained by condensation of the appropriate 1-aryl-1,2,3,-butanetrione-2-oxime and an appropriate dialkyl acetonedicarboxylate as starting materials to provide the corresponding ring closed pyrrole, alkyl 5-aroyl-3-alkoxycarbonyl-4-methylpyrrole-2-acetate; or by condensation of an appropriate chloromethyl lower alkyl ketone added to a mixture of an appropriate diloweralkyl acetonedicarboxylate, preferably the diethyl ester and a lower alkyl amine to provide the ring-closed pyrrole, alkyl 1,4-diloweralkyl-3-alkoxycarbonyl pyrrole-2-acetate. These pyrrole intermediates are then treated as disclosed in U.S. Pat. Nos. 3,752,826 and 3,865,840 to obtain the desired 5-aroyl-4-lower alkyl-pyrrole-2-alkanoic acids and acid derivatives thereof useful as anti-inflammatory agents.

The condensation of chloromethylketone, ammonia and hydroxy crotonic acid alkylester through an anticrotonic acid ester is taught by Fischer and Orth, *Die Chemie Des Pyrroles*, pp. 5–6, and 233–234, Edward Brothers, Inc., Ann Arbor, Mich., 1943. However, neither the 4-alkyl-substituent nor the diester functionality are disclosed in this reference.

Another pyrrole ring-closure synthesis, known as the Hantzsch pyrrole synthesis, teaches the interaction of alphachloro-aldehydes or ketones with beta-ketoesters and ammonia or amines to give pyrroles, Gowan and Wheeler, *Name Index of Organic Reactions*, p. 116. Longmans, Green and Co., Ltd., New York, N.Y., 1960.

In a similar manner, there is taught the reaction of chloroacetone with a salt produced from reaction of methylamine and diethyl acetone dicarboxylate to give a 4-methylpyrrole, Jones and Bean, *The Chemistry of Pyrroles*, pp. 59, 104, Academic Press, Inc., New York, 1977. Also, the pyrrole synthesis from chloromethyl ketones and beta-ketocarboxylic esters with ammonia or amines is known, Krauch and Kunz, *Organic Name Reactions*, p. 211, John Wiley and Sons, Inc., New York, 1964. However, such teachings either fail to suggest the possibility of the pyrrole diester compounds or teach no more than Carson, supra, and are based thereon.

Specifically pertinent to the improved process of this invention, U.S. Pat. Nos. 3,752,826 and 3,865,840 teach that after reaction of, for example, aqueous methylamine with diethyl acetone dicarboxylate and then adding chloroacetone at a temperature just below 60° C. for a period of two hours, the resultant reaction mixture is poured into ice-hydrochloric acid. The acidification acts to dehydrate the intermediate dihydroxy pyrrolidine to the desired pyrrole. However, the reaction forms solid intermediates which are difficult to agitate and conversion of the intermediates to the desired product results in an exothermic reaction which is difficult to control on a large scale. In an attempt to overcome the solids formation problem, the reaction of diethyl acetone dicarboxylate with chloroacetone and aqueous methylamine was carried out in the presence of an added co-solvent, e.g., a halogenated hydrocarbon, such as methylene chloride, or an aromatic hydrocarbyl compound, such as toluene, at temperatures from 25° C. to 40° C. by Messrs. Dagani and Kao, respectively, as described in patent applications Ser. Nos. 137,231 and 137,250 now pending, both filed on Apr. 4, 1980. Further, it was discovered by Messrs. Kao and Farritor that when conducting the reaction at even lower temperatures, say from 0° C. to about 15° C., that even in the presence of an added co-solvent, such as methylene chloride, solids formation with its attendant lower contacting and mixing problems could occur. It was, however, discovered by Messrs. Kao and Farritor that the addition to the reaction mixture of a lower alkanol having from 1 to about 6 carbon atoms served to aid the dissolution of solids formed in the reaction mixture at temperatures down to about 0° C. as described in patent application Ser. No. 239,431 filed on Mar. 2, 1981.

In U.K. patent application No. GB 2,034,304 A there is disclosed a process for producing a substituted pyrrole of the formula:

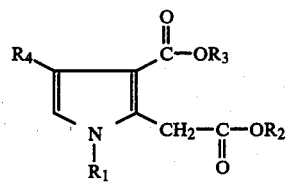

wherein R₁ is a hydrocarbyl group of up to about 20 carbon atoms, R₂ and R₃ are independently alkyl or aralkyl of up to about 20 carbon atoms and R₄ is H or a hydrocarbyl of up to about 20 carbon atoms which comprises reacting a primary amine R₁NH₂ with an acetone dicarboxylic acid diester:

and a substituted carbonyl compound R₄COCH₂X where X is a leaving group. The pyrrole forming reaction is conducted in a two-phase aqueous/organic reaction medium dispersion containing R₁NH₂ with which the acetone dicarboxylic acid ester and substituted carbonyl compound are combined and/or in a reaction medium containing R₁NH₂ to which the acetone dicarboxylic acid ester and substituted carbonyl compounds are added in a substantially simultaneous manner.

In patent application Ser. No. 137,511, now pending, filed Apr. 4, 1981, there is described a method for obtaining the desired loweralkyl 1,4-diloweralkyl-3-loweralkoxycarbonyl-pyrrole-2-acetate by adding chloromethylloweralkyl ketone to a pre-mixed cooled solution of aqueous loweralkylamine and a diloweralkyl acetone dicarboxylate in a suitable solvent with reaction at below 60° C., and heating the resultant reaction mixture to from about 70° C. to 100° C. for a period of time sufficient to dehydrate the dihydroxy pyrrolidine intermediate in the resultant reaction mixture and produce the desired loweralkyl 1,4-diloweralkyl-3-loweralkoxycarbonyl-pyrrole-2-acetate.

The Invention

In a search for improved processes for the reaction of a loweralkylamine in aqueous solution with a diloweralkyl acetone dicarboxylate, it has now been discovered that the formation of solids can be controlled, i.e., reduced and/or prevented from forming, by reacting a diloweralkyl acetone dicarboxylate with a substituted carbonyl compound such as chloroacetone and methylamine in a non-aqueous reaction medium. The utilization of a single-phase non-aqueous reaction medium not only overcomes the solids formation problem, but also simplifies the reaction procedure and permits better feed control particularly in contrast to conducting the reaction in the presence of an aqueous/organic two-phase system such as the process disclosed in aforementioned U.K. patent application No. GB 2,034,304 A.

Accordingly, the present invention provides a process for the preparation of a loweralkyl 1,4-diloweralkyl-3-loweralkoxy-carbonyl-pyrrole-2-acetate of the formula:

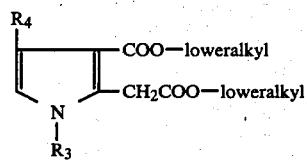

by reacting in a solvent a chloromethyl loweralkyl ketone of the formula: Cl—CH₂—CO—R₄, with a diloweralkyl acetone dicarboxylate of the formula:

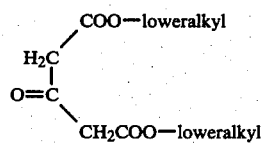

and anhydrous loweralkylamine of the formula: R₃NH₂, wherein the foregoing formulas said R₃ and said R₄ represent loweralkyl.

As used in this invention, "loweralkyl" and "loweralkoxy" may be straight or branched chain saturated hydrocarbons having from 1 to 6 carbon atoms, such as, for example, methyl, ethyl, propyl, isobutyl, isopropyl, butyl, pentyl, hexyl and the like alkyls and, repsectively, the corresponding alkoxys such as methoxy, ethoxy, propoxy, isopropoxy, and the like.

The loweralkoxy 1,4-diloweralkyl-3-loweralkoxycarbonyl-pyrrole-2-acetate of the present invention is preferably produced when the chloromethyl loweralkyl ketone is a chloroacetone. Chloroacetone is a readily available and relatively inexpensive ketone. The dicarboxylate is preferably dimethyl or diethyl acetone dicarboxylate which can be prepared according to known procedures. The other reactant is a lower-alkylamine, preferably methylamine in order to have a 1-methylpyrrole compound produced. Should other 1-substituted pyrroles be desired, then other amines such as aryl amines or other alkyl amines, are also suitable reactants in the process of this invention. However, preferably, in order to produce the 1,4-diloweralkyl pyrrole compound, methylamine is used.

As indicated hereinabove, it has been found that the use of non-aqueous methylamine has certain advantages. For one, since gaseous methylamine is simply added to the reaction mixture by condensing in or pressuring in methylamine, feed control is much better than in those systems using an aqueous reaction medium. This is particularly true in scale-up operations. Further, comparable yields with prior art processes are obtained while inhibition of solids formation during the addition of methylamine allows more efficient agitation which is conducive to good reactant contact, better heat distribution, more effective process control and requires less power for agitation.

The solvent employed in the process of this invention is an inert, organic solvent with a high degree of solubility for the dialkyl acetone dicarboxylate and the cyclized, substituted pyrrole product. Several types of organic solvents may be suitable for use in the present process. Typically, organic solvents which are aromatic hydrocarbon compounds, aliphatic hydrocarbon compounds, halogenated aromatic and aliphatic hydrocarbon compounds and the like which have boiling points from about 30° C. to about 200° C. at normal pressures are particularly suitable because such solvents in addition to preventing solids formation by solubilizing reactants and products also provide a method of convenient heat removal by operation at reflux. Specifically, chlorinated and brominated hydrocarbon solvents such as carbontetrachloride, carbontetrabromide, chloroform, bromoform, methylene chloride, methylene bromide, tetrachloroethane, ethylenedichloride, ethylene dibromide, chlorobenzene, bromobenzene, o-dichlorobenzene and the like are examples of useful solvents. Further, simple aromatic hydrocarbons, such as benzene, xylene and toluene are likewise useful and practical solvents in the process of the present invention. Of particular preference, methylene chloride provides the combined properties of solubility, heat removal, sufficient inertness to the reactants and products and low cost for best results in the present process. Although methylene chloride is preferred, any solvent having similar advantageous properties can be used.

The reaction of, for example, diethyl acetone dicarboxylate, methylamine and chloroacetone is carried out by charging methylene chloride to a reactor and then condensing in or pressuring in anhydrous methylamine at about 0° C. to about 30° C. A mixture of acetone dicarboxylic acid ester, substituted carbonyl compound, i e., chloroacetone, and methylene chloride are then combined with the methylamine containing methylene chloride reaction medium. Reflux is maintained with reaction temperatures ranging from about 15° C. to about 65° C., preferably from about 20° C. to about 40° C. conveniently using a dry ice condenser. The reaction is conducted for a period of time sufficient to complete the reaction and then the resultant solution is acidified or thermally dehydrated to form the pyrrole product. Reaction time may vary from approximately 0.5 to 2.0 hours.

Although the most preferred and advantageous results occur with the process of this invention at reaction temperatures in the range of approximately 15° C. to about 65° C., the reaction can be carried out at temperatures higher than 65° C. if, for example, shorter reaction times are desired. However, at temperatures in considerable excess of 65° C. yields would be expected to drop off. In contrast, at temperatures below about 15° C., a solid intermediate forms. Such an intermediate solid compound is most likely the methylammonium salt of the acetone dicarboxylic acid ester anion:

Alternatively, the reaction may be carried out by charging methylene chloride to a reaction vessel and then adding sequentially to the vessel a mixture of acetone dicarboxylate in methylene chloride, a mixture of anhydrous methylamine in methylene chloride and a mixture of chloroacetone in methylene chloride.

To ensure adequate yields of the desired substituted pyrrole diester product, the primary amine and substituted carbonyl compound should be employed in stoichiometric excess vis-a-vis the acetone dicarboxylate. In general, the molar ratio of primary amine to acetone dicarboxylate can range from about 3:1 to about 10:1, and preferably is about 6:1. Generally, the molar ratio of substituted carbonyl compound to acetone dicarboxylate can range from about 1:1 to about 2:1. The molar ratio of methylene chloride to acetone dicarboxylate generally ranges from about 5:1 to about 30:1, and preferably from about 8:1 to about 15:1.

When a mixture of acetone dicarboxylate, substituted carbonyl compound and methylene chloride are introduced into the amine containing-methylene chloride reaction medium, the molar ratio of substituted carbonyl compound to acetone dicarboxylate combined with the reaction medium will generally range from about 1.3:1 to about 1.6:1 during the time period in which these reactants are being combined with the reaction medium. The molar ratio of methylene chloride to acetone dicarboxylate in the mixture to be combined with the reaction medium will generally range from about 6:1 to about 10:1. The molar ratio of methylamine to methylene chloride in the reaction medium will generally range from about 1:1 to about 1:3 when this method of addition is used.

The simultaneous reactant addition of ester and substituted carbonyl compound, of course, includes the situation wherein the acetone dicarboxylate and substituted carbonyl compound are separately and continuously fed to the reaction vessel using feed rates such that the requisite molar ratio of these two reactants is maintained during reactant addition. Substantially simultaneous reactant addition can also include the situation wherein the acetone dicarboxylate and substituted carbonyl reactants are added in pairs of discrete increments or "shots," provided the molar ratio of the total amounts of each reactant added does not fall outside the 1.3:1 to 1.6:1 range. At least some and preferably all of the primary amine reactant is present in the reaction medium before a substantially simultaneous addition of the other two reactants is begun.

Upon addition of the acetone dicarboxylate to the reaction medium containing primary amine, a white precipitate intermediate compound is generally formed. Such an intermediate compound is possibly an amine salt of the acetone dicarboxylate ester. Further reaction of this intermediate compound with the substituted carbonyl compound such as chloroacetone eventually produces the desired substituted pyrrole diester. Since the intermediate compound appears to decompose with time, the substantially simultaneous addition of acetone dicarboxylate and substituted carbonyl compound is believed to enhance pyrrole diester production by promoting reaction of the intermediate before it decomposes. The simultaneous reaction addition feature of the present invention is thus especially effective in maintaining an acceptably high product yield in large batch, high throughput, commercial scale processes wherein control of the condensation/cyclization reaction exotherm necessitates extended reactant addition procedures and longer reaction times.

The reaction medium employed in the present invention is generally agitated and cooled throughout the reaction. Agitation should be sufficient to form a uniform dispersion containing whatever small amounts of solids, thought to be methylamine hydrochloride, that may form during the reaction.

After the reaction has been completed, various procedures to recover, purify and/or further treat the desired substituted pyrrole ester product can be undertaken. After the pyrrole ester is formed but before agitation is discontinued, for example, the reaction medium can be acidified, for example, with HCl in order to eliminate excess organic amine reactants and/or by-products. Alternatively, the temperature in the reaction vessel can be increased after completion of the reaction to distill off the aforementioned excess organic amine reactants and/or by-products and the organic solvent, e.g., methylene chloride, used in the reaction. After acid treatment or during distillation, water is added to the resultant solution to dissolve the methylamine hydrochloride which may have formed during the reaction. This can also be done at room temperature. Alternatively the solid methylamine hydrochloride can be separated from the product-containing solution by filtration. After distillation, the desired pyrrole ester is then extracted from the resultant reaction mixture by adding a suitable extraction solvent to the mixture. Suitable solvents which may be used are aromatic hydrocarbon compounds, aliphatic hydrocarbon compounds, halogenated aromatic and aliphatic hydrocarbon compounds and the like which have boiling points from about 30° C. to about 200° C. at normal pressures. Specifically, chlorinated and brominated hydrocarbon solvents such as carbontetrachloride, carbontetrabromide, chloroform, bromoform, methylene chloride, methylene bromide, tetrachloroethane, ethylenedichloride, ethylene dibromide, chlorobenzene, bromobenzene, o-dichlorobenzene and the like are examples of useful solvents. Further, simple aromatic hydrocarbons, such as benzene, xylene and toluene are likewise useful and practical solvents in the process of the present invention. Of particular preference is toluene.

If an essentially pure pyrrole diester product is desired, the organic solvent can be stripped from the pyrrole ester and the pyrrole ester recrystallized from a suitable solvent.

The following examples are given solely for the purpose of illustration and are not to be construed as limitations of this invention.

EXAMPLE 1

To a 250 ml three-neck round bottom flask fitted with a dry ice chilled cold finger condenser, mechanical agitator and feed nozzle was added 34.0 g (0.40 mole) of methylene chloride and chilled to 5° C. Anhydrous methylamine, 7.46 g (0.240 mole) was then condensed into the reaction flask. The mixture was then agitated and a mixture of 8.57 g (0.040 mole) acetone dicarboxylate, 5.82 g (0.056 mole) chloroacetone and 17.0 g (0.20) methylene chloride was fed into the flask below the surface of the contents in the flask over a period of time of approximately 37 minutes. The 5° C. water bath was slowly allowed to warm up. Heavy solids formed after 15 minutes and the temperature was raised to 25° C. at which point the solids disappeared. The reaction temperature was then raised to 35.5° C. and the reaction allowed to progress for about 30 minutes at a temperature between about 30° C. and 35° C. The temperature was then raised to about 95.5° C. over a period of time of approximately 25 minutes to distill off excess amine reactants and/or by-products and methylene chloride. The temperature was then lowered to approximately 85° C. and 12 g of water was added to the resultant reactant medium to dissolve the small amounts of methylamine hydrochloride that had formed during the reaction. The product ester was extracted from the medium twice with 25 g and 10 g of toluene, respectively. Analysis by VPC indicated a 68% yield of ethyl 1,4-dimethyl-3-ethoxycarbonylpyrrole-2-acetate.

In a similar manner, several other experiments were carried out varying the amounts of reactants and reaction conditions to study the effect of using anhydrous methylamine to make ethyl 1,4-dimethyl 2-ethoxycarbonylpyrrole-2-acetate with the results being given in the following table.

TABLE

Preparation of Ethyl 1,4-Dimethyl-3-ethoxycarbonylpyrrole-2-acetate (PDE) by Reaction of Diethyl Acetone Dicarboxylate (ADC), Chloroacetone (CA) and Anhydrous Methylamine (MA) in Methylene Chloride (CH$_2$Cl$_2$)

| Example No. | MA/ADC | CH$_2$Cl$_2$/ADC | CA/ADC | Temp., °C. | PDE Yield, % |
|---|---|---|---|---|---|
| 2 | 5 | 15 | 1.38 | 15 | 15.5 |
| 3 | 5 | 13.4 | 1.38 | 20 | 67 |
| 4 | 2.4 | 15 | 1.4 | 30 | 28.5 |
| 5 | 5 | 10.7 | 1.38 | 15 | 57 |
| 6 | 5 | 15 | 1.38 | 15 | 62 |
| 7 | 5 | 15 | 1.38 | 15 | 64.5 |
| 8 | 6 | 15 | 1.4 | 25 | 68 |
| 9 | 6 | 15 | 1.4 | 30 | 64 |
| 10 | 6 | 15 | 1.4 | 30 | 66.5 |
| 11 | 6 | 15 | 1.4 | 30 | 67 |
| 12 | 6 | 15 | 1.4 | 35 | 65.5 |
| 13 | 6 | 15 | 1.4 | 38 | 68.5 |
| 14 | 6 | 13.5 | 1.4 | 30 | 62 |
| 15 | 6 | 14 | 1.4 | 25 | 72 |

Molar Ratio of[1]

[1]10 moles CH$_2$Cl$_2$ fed with ADC; remainder with MA.

Having disclosed the process of the invention, one skilled in the art can readily envision variations, modifications and changes within the scope and spirit of this invention. Therefore, it is desired that the present invention be limited only by the lawful scope of the following claims.

We claim:

1. In a process for preparing a loweralkyl 1,4-diloweralkyl-3-loweralkoxycarbonylpyrrole-2-acetate corresponding to the formula:

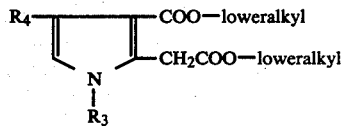

by reacting a chloromethyl loweralkyl ketone of the formula ClCH$_2$COR$_4$ with a diloweralkyl acetone dicarboxylate of the formula:

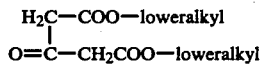

and an anhydrous loweralkylamine of the formula R$_3$NH$_2$, in which formulas R$_3$ and R$_4$ represent loweralkyl, the improvement which comprises contacting the reactants in a single-phase non-aqueous reaction medium.

2. The process of claim 1 wherein the reaction medium is methylene chloride.

3. The process of claim 1 wherein the chloromethyl loweralkyl ketone is chloroacetone.

4. The process of claim 1 wherein the loweralkylamine is methylamine.

5. The process of claim 1 wherein the dicarboxylate is diethyl acetone dicarboxylate.

6. The process of claim 1 wherein the dicarboxylate is diethyl acetone dicarboxylate, the loweralkylamine is methylamine and the ketone is chloroacetone.

* * * * *